United States Patent
Hembrough et al.

(10) Patent No.: US 10,725,045 B2
(45) Date of Patent: Jul. 28, 2020

(54) QUANTIFYING MGMT PROTEIN FOR OPTIMAL CANCER THERAPY OF GLIOBLASTOMA

(71) Applicant: NantOmics, LLC, Culver City, CA (US)

(72) Inventors: Todd A. Hembrough, Gaithersburg, MD (US); Fabiola Cecchi, Potomac, MD (US); Dongyao Yan, Rockville, MD (US)

(73) Assignee: NantOmics, LLC, Culver City, CA (US)

(*) Notice: Subject to any disclaimer, the term of this patent is extended or adjusted under 35 U.S.C. 154(b) by 0 days.

(21) Appl. No.: 16/273,341

(22) Filed: Feb. 12, 2019

(65) Prior Publication Data
US 2019/0265242 A1  Aug. 29, 2019

Related U.S. Application Data

(60) Provisional application No. 62/630,226, filed on Feb. 13, 2018.

(51) Int. Cl.
| | |
|---|---|
| *G01N 33/574* | (2006.01) |
| *A61K 31/4188* | (2006.01) |
| *A61K 31/495* | (2006.01) |
| *A61P 35/00* | (2006.01) |
| *G01N 33/50* | (2006.01) |

(52) U.S. Cl.
CPC ... *G01N 33/57407* (2013.01); *A61K 31/4188* (2013.01); *A61K 31/495* (2013.01); *A61P 35/00* (2018.01); *C12Y 201/01063* (2013.01); *G01N 33/5088* (2013.01); *G01N 33/57484* (2013.01); *G01N 2333/91017* (2013.01)

(58) Field of Classification Search
CPC ... A61K 31/4188; A61K 31/495; A61P 35/00; C12Y 201/01063; G01N 2333/91017; G01N 33/5088; G01N 33/57407; G01N 33/57484
See application file for complete search history.

(56) References Cited

U.S. PATENT DOCUMENTS

| | | | |
|---|---|---|---|
| 7,473,532 B2 | 1/2009 | Darfler et al. | |
| 9,765,380 B2 | 9/2017 | Krizman | |
| 10,060,927 B2* | 8/2018 | Krizman | C12Q 1/48 |
| 2019/0353658 A1* | 11/2019 | Hembrough | G01N 33/6848 |

FOREIGN PATENT DOCUMENTS

| | | |
|---|---|---|
| WO | WO-2008154590 A2 | 12/2008 |
| WO | WO-2014037977 A1 | 3/2014 |

OTHER PUBLICATIONS

ExPASy—PeptideCutter for MGMT_Human (P26455) from UNiProtKB/Swiss-Prot, accessed online at https://web.expasy.org/cgi-bin/peptide_cutter/peptidecutter.pl on Dec. 9, 2019. 2 pages (Year: 2019).*

Yi et al. Acquired temozolide resistance in MGMT-deficient glioblastoma cells is associated withregulation of DNA repair by DHC2. Brain 2019, vol. 142, pp. 2352-2366. (Year: 2019).*

Extended European Search Report from European Application No. EP 19156939.1 dated Jul. 2, 2019.

Yan D., et al., "Comp-16. Correlating MGMT Protein Level with Temozolomide Response in Glioblastoma Patients Using Mass Spectrometry," Neuro-Oncology, 20(6): 1-4 (2018).

Schwartz S., et al., "Selecting Patients with metastatic colorectal cancer for treatment with temozolomide using proteomic analysis of MGMT," Journal of Clinical Oncology, 35(15): 1-4 (2017).

Sevim H., et al., "Abstract 5094: Protein biomarker discovery in glioblastoma using Seldi-Tof-MS," Cancer Research (2011).

* cited by examiner

*Primary Examiner* — Marcela M Cordero Garcia
(74) *Attorney, Agent, or Firm* — Harness Dickey & Pierce P.L.C.

(57) ABSTRACT

Methods are provided for treating a cancer patient suffering from a glioblastoma (GBM) by administering to the patient an effective amount of temozolomide, wherein a mass spectrometry analysis of a protein digest of a formalin-fixed tumor sample from the patient evidences an amount of a MGMT fragment peptide less than or substantially equal to 150 amol/μg.

16 Claims, 1 Drawing Sheet
Specification includes a Sequence Listing.

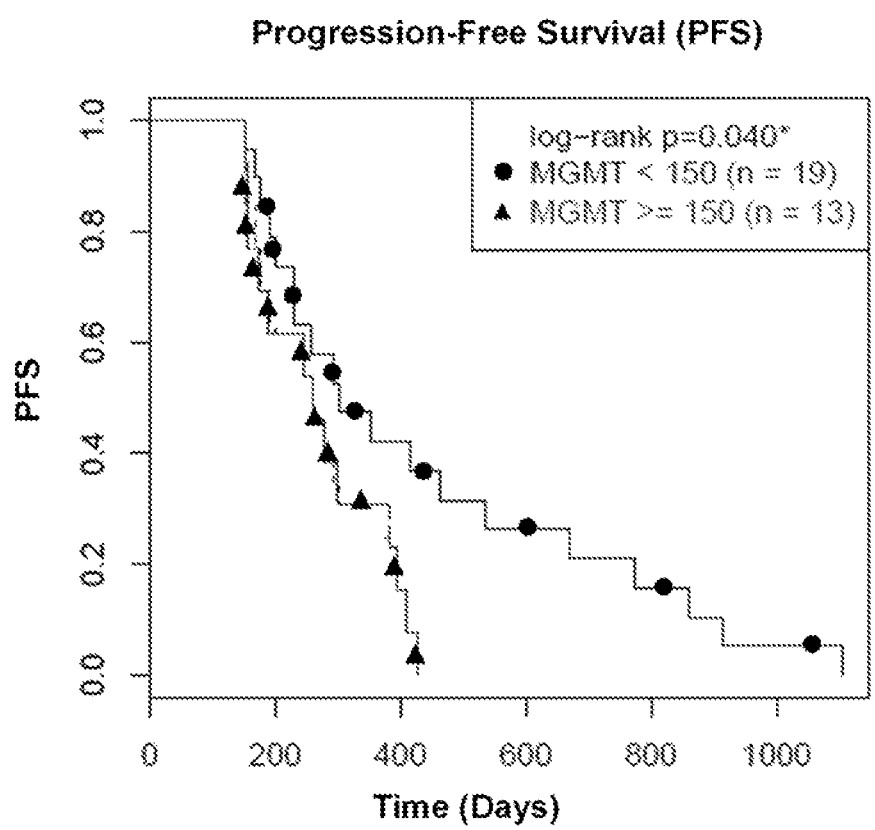

QUANTIFYING MGMT PROTEIN FOR OPTIMAL CANCER THERAPY OF GLIOBLASTOMA

CROSS-REFERENCED APPLICATIONS

This application claims the benefit of U.S. Provisional Application No. 62/630,226 filed on 13 Feb. 2018, the entire contents of which are hereby incorporated by reference.

FIELD

Methods are provided for treating cancer patients, particularly glioblastoma cancer, by assaying tumor tissue from patients and identifying those patients most likely to respond to treatment with the anti-cancer drug temozolomide (TMZ).

BACKGROUND

Glioblastoma (GBM) is a tumor of the brain and represents about 15.4% of all primary brain tumors and about 60-75% of all astrocytomas. GBM tumors increase in frequency with age, and affect more men than women. Only three percent of childhood brain tumors are glioblastomas. Standard fluorouracil-based chemotherapy can prolong survival but most patients eventually become resistant. The chemotherapy drug TMZ is standard treatment for patients with GBM. TMZ, also known as Temodar®, is an oral chemotherapy drug in the class of alkylating agent which also includes such chemotherapy agents as cisplatin, carboplatin, cyclophosphamide, melphalan and chlorambucil.

In multiple cancer types, the DNA repair protein 06-methylguanine-DNA methyl-transferase (MGMT) is a resistance marker for TMZ because it is thought that MGMT promoter methylation is associated with loss of MGMT expression and response to TMZ. The therapeutic benefit of TMZ, and other alkylating agents, depends on its ability to alkylate/methylate DNA resulting in damage to the DNA thus triggering the death of tumor cells. However, alkylating antineoplastic agents have limitations based on the fact that some tumor cells are able to repair this type of DNA damage therefore diminishing the therapeutic efficacy of TMZ. Cross-linking of double-stranded DNA by alkylating agents is inhibited by the cellular DNA-repair protein MGMT. In some tumors, epigenetic silencing of the MGMT gene prevents the synthesis of this enzyme, and as a consequence such tumors are more sensitive to killing by TMZ. Conversely, the presence of MGMT protein in tumors cells may predict poor response to TMZ and these patients receive little benefit from chemotherapy with TMZ. Thus there is a need for improved methods of treating cancers, such as gliobastoma, with TMZ by using new and improved methods of easily and accurately determining MGMT biomarker levels in patient samples.

SUMMARY

The improved methods of cancer treatment described herein identify cancer patients, particularly glioblastoma patients, who are most likely to respond to treatment with administration of TMZ by determining levels of the MGMT protein directly in a patient tumor tissue sample via SRM/MRM mass spectrometry.

In particular embodiments, the patient tumor tissue sample is a formalin-fixed tissue sample, such as formalin-fixed paraffin embedded (FFPE) tissue.

In yet additional embodiments, the FFPE tissue is protein digested and analyzed by SRM/MRM mass spectrometry.

BRIEF DESCRIPTION OF THE DRAWINGS

FIG. 1 is a graphical representation of progression-free survival (PFS) vs. time (days) in patients whose tumor cells expressed the MGMT protein above or below 150 amol/µg of tumor cell protein when treated with TMZ.

DETAILED DESCRIPTION

Improved methods for treating cancer are provided by determining if a cancer patient will clinically respond in a favorable manner to the therapeutic cancer agent TMZ. Specifically, diagnostic methods for measuring the quantitative level of the MGMT protein in a tumor sample or samples from the patient are provided. In one embodiment, a mass spectroscopy assay, such as an SRM/MRM assay, can be used to measure a specified MGMT peptide fragment, providing a measure of the amount of the MGMT protein in cells derived from formalin-fixed paraffin embedded (FFPE) tissue. One peptide molecule can derive from one protein molecule and thus measurement of the molar amount of the peptide provides a direct measure of the molar amount of the protein. See U.S. patent application Ser. No. 13/993,045, the contents of which are hereby incorporated by reference in their entirety. In a particular embodiment, the MGMT peptide fragment derives from the full-length MGMT protein, wherein the peptide sequence is TTLDSPLGK (SEQ ID NO:1). Surprisingly it has been found that this peptide fragment can be reliably detected and quantitated in protein digests prepared from FFPE samples of tumor tissue.

More specifically, these SRM/MRM assays can measure this peptide directly in complex protein lysate samples prepared from cells procured from patient tissue samples, such as formalin-fixed cancer patient tissue. The most widely and advantageously available form of tissue, and cancer tissue, from cancer patients is formalin-fixed, paraffin embedded tissue. Formaldehyde/formalin fixation of surgically removed tissue is by far the most common method of preserving cancer tissue samples worldwide and is the accepted convention in standard pathology practice. Aqueous solutions of formaldehyde are referred to as formalin. "100%" formalin consists of a saturated solution of formaldehyde (about 40% by volume or 37% by mass) in water, with a small amount of stabilizer, usually methanol, to limit oxidation and degree of polymerization. The most common way in which tissue is preserved is to soak whole tissue for extended periods of time (8 hours to 48 hours) in aqueous formaldehyde, commonly termed 10% neutral buffered formalin, followed by embedding the fixed whole tissue in paraffin wax for long-term storage at room temperature. Thus molecular analytical methods to analyze formalin-fixed cancer tissue will be the most accepted and heavily utilized methods for analysis of cancer patient tissue.

Further, methods of preparing protein samples from formalin-fixed tissue, such as FFPE tissue, are described in U.S. Pat. No. 7,473,532, the contents of which are hereby incorporated by reference in their entirety. The methods described in U.S. Pat. No. 7,473,532 may conveniently be carried out using Liquid Tissue™ reagents and protocol available from Expression Pathology Inc. (Rockville, Md.). For example, a composition comprising the formalin-fixed tumor sample and a reaction buffer can be heated at a temperature from 80° C. to 100° C. for a period of time from 10 minutes to 4 hours. Additionally, the resulting composition can be treated with an effective amount of a proteolytic enzyme selected from the group consisting of trypsin, chymotrypsin, and endoproteinase Lys-C for a period of time from 30 minutes to 24 hours at a temperature from 37° C. to 65° C. In a particular embodiment, the proteolytic enzyme is trypsin.

Results from the SRM/MRM assay can be used to correlate accurate and precise quantitative levels of the MGMT protein within the specific cancer of the patient from whom the tissue was collected and preserved, including colon, skin, and brain cancer tissue. This not only provides diagnostic information about the cancer, but also permits a physician or other medical professional to determine appropriate therapy for the patient. In this case, utilizing this assay can provide information about specific levels of MGMT protein expression in cancer tissue and whether or not the patient from whom the cancer tissue was obtained will respond in a favorable way to therapy with the anti-cancer therapeutic agent TMZ, and potentially other similar drugs in the alkylating agent class designed to specifically damage DNA in tumor cells.

Treating cancer patients with TMZ is one of the most common and effective strategies for preventing cancer from growing and thus prolonging the lives of cancer patients, especially brain, skin, and colon cancer patients. The MGMT protein is a protein that repairs damaged DNA, and more specifically repairs the type of damage inflicted by the anti-cancer therapeutic agent TMZ, and other similar alkylating agents. Thus if there is MGMT protein present in a tumor cell that is being treated with TMZ, and/or other similar alkylating agents, the DNA will be constantly repaired and thus provide chemotherapy resistance to the tumor cell and the tumor cell will likely not be killed.

It therefore is useful for a clinician to know the presence or absence or level of the MGMT protein in a patient's cancer cells because the effects of TMZ, and/or other similar alkylating agents, will be negated and the cancer patient will not respond to TMZ, and/or other similar alkylating agents.

Presently the most widely-used and applied methodology to determine protein presence in cancer patient tissue, especially FFPE tissue, is immunohistochemistry (IHC). IHC methodology utilizes an antibody to detect the protein of interest. The results of an IHC test are most often interpreted by a pathologist or histotechnologist. This interpretation is subjective and does not provide quantitative data that can be predictive of temozolomide sensitivity or resistance.

Research from other IHC assays, such as the Her2 IHC test, suggest the results obtained from such tests may be wrong or misleading. This is probably because different labs use different rules for classifying positive and negative IHC status. Each pathologist running the tests also may use different criteria to decide whether the results are positive or negative. In most cases, this happens when the test results are borderline, meaning that the results are neither strongly positive nor strongly negative. In other cases, tissue from one area of cancer tissue can test positive while tissue from a different area of the cancer tests negative. Inaccurate IHC test results may mean that patients diagnosed with cancer do not receive the best possible care. If all or part of a cancer is positive for a specific target oncoprotein but test results classify it as negative, physicians are unlikely to recommend the correct therapeutic treatment, even though the patient could potentially benefit from those agents. If a cancer is oncoprotein target negative but test results classify it as positive, physicians may recommend a specific therapeutic treatment, even though the patient is unlikely to get any benefits and is exposed to the agent's secondary risks.

Accordingly, there is great clinical value in the ability to correctly evaluate quantitative levels of the MGMT protein in tumors, especially brain, skin, and colon tumors, so that the patient will have the greatest chance of receiving the correct chemotherapy and, in particular, whether the patient is treated with TMZ, and/or other similar alkylating agents.

Thus, the presence and/or quantitative levels of MGMT protein expression in cells within tumor tissue can be determined by quantitating a specified peptide derived from subsequences of the full-length MGMT protein (also referred to $O^6$-alkylguanine DNA alkyltransferase, AGT, MGMT or AGAT). If expression of the MGMT protein is below a specified quantitative level, the patient can be treated with a regimen that includes the TMZ therapeutic agent, and other drugs that function similarly to TMZ Conversely, if the MGMT level is above the specified quantitative level, the patient can be treated with a regimen that does not include TMZ nor other drugs that function similar to TMZ, such as cisplatin, carboplatin, oxaliplatin, cyclophosphamide, melphalan and/or chlorambucil. This allows specific and optimized therapeutic agents and treatment strategies to be used to treat an individual cancer patient's disease based on how much of the MGMT protein is present in their cancer cells.

Detecting and determining quantitative levels of the specified MGMT fragment peptide is performed in a mass spectrometer by the SRM/MRM methodology, whereby the SRM/MRM signature chromatographic peak area of the peptide is determined within a complex peptide mixture present in a Liquid Tissue™ lysate (see U.S. Pat. No. 7,473,532, as described above). Quantitative levels of the MGMT protein are then determined by the SRM/MRM methodology whereby the SRM/MRM signature chromatographic peak area of an individual specified peptide from the MGMT protein in one biological sample is compared to the SRM/MRM signature chromatographic peak area of a known amount of a "spiked" internal standard for the individual MGMT fragment peptide. In one embodiment, the internal standard is a synthetic version of the same exact MGMT fragment peptide where the synthetic peptide contains one or more amino acid residues labeled with one or more heavy isotopes. Such isotope labeled internal standards are synthesized so that mass spectrometry analysis generates a predictable and consistent SRM/MRM signature chromatographic peak that is different and distinct from the native MGMT fragment peptide chromatographic signature peaks and which can be used as comparator peaks. Thus when the internal standard is spiked in known amounts into a protein or peptide preparation from a biological sample and analyzed by mass spectrometry, the SRM/MRM signature chromatographic peak area of the native peptide is compared to the SRM/MRM signature chromatographic peak area of the internal standard peptide, and this numerical comparison indicates either the absolute molarity and/or absolute weight of the native peptide present in the original protein preparation from the biological sample. Quantitative data for fragment peptides are displayed according to the amount of protein analyzed per sample.

In order to develop the SRM/MRM assay for the MGMT fragment peptide additional information beyond simply the peptide sequence may be utilized by the mass spectrometer. That additional information may be used to direct the mass spectrometer, (e.g., a triple quadrupole mass spectrometer) to perform the correct and focused analysis of the specified MGMT fragment peptide. A triple quadrupole mass spectrometer is a particularly suitable instrument for analyzing a single isolated target peptide within a very complex protein lysate that may consist of hundreds of thousands to millions of individual peptides from all the proteins contained within a cell. The additional information provides the triple quadrupole mass spectrometer with the correct directives to allow analysis of a single isolated target peptide within a very complex protein lysate that may consist of hundreds of thousands to millions of individual peptides from all the proteins contained within a cell. Although the most advantageous instrument platform for SRM/MRM assay is often considered to be a triple quadrupole instrument platform, SRM/MRM assays can be developed and performed on any type of mass spectrometer, including a MALDI, ion trap, ion trap/quadrupole hybrid, or triple quadrupole. The additional information about target peptides in general, and in particular about the specified MGMT fragment peptide (SEQ ID NO:1), may include one or more of the mono isotopic mass of each peptide, its precursor charge state, the precursor m/z value, the m/z transition ions, and the ion type of each transition ion. The peptide sequence of the specified MGMT fragment peptide and the necessary additional information as described for these specified MGMT fragment peptide is shown in Table 1.

TABLE 1

| SEQ ID NO | Peptide Sequence | Mono Iso-topic Mass | Pre-cursor Charge State | Pre-cursor m/z | Trans-ition m/z | Ion Type |
|---|---|---|---|---|---|---|
| 1 | TTLDSPLGK | 930.5021 | 2 | 466.258 | 414.27 | Y4 |
|   |           |          | 2 | 466.258 | 616.329 | Y6 |
|   |           |          | 2 | 466.258 | 729.413 | Y7 |

To determine an appropriate reference level for MGMT quantitation, tumor samples were obtained from a cohort of patients suffering from cancer, in this case GBM. The GBM tumor samples were formalin-fixed using standard methods and the level of MGMT in the samples was measured using the methods as described above. The tissue samples may also be examined using IHC and FISH using methods that are well known in the art. The patients in the cohort were treated with the temozolomide therapeutic agent and the response of the patients was measured using methods that are well known in the art, for example by recording the progression-free survival and overall survival of the patients at time intervals after treatment. A suitable reference level was determined using statistical methods that are well known in the art, for example by determining the lowest p value of a log rank test. Once a reference level has been determined it can be used to identify those patients whose MGMT expression levels indicate that they may likely benefit from a temozolomide therapeutic regimen. The skilled artisan will recognize that temozolomide is also used as part of a treatment regimen that utilizes additional drugs or combinations of drugs, such as in combination with an inhibitor of the EGFR protein. Levels of the MGMT protein in patient tumor samples are typically expressed in amol/µg, although other units can be used. The skilled artisan will recognize that a reference level can be expressed as a range around a central value, for example, +/−250, 150, 100, 50 or 25 amol/µg. In the specific example described in detail below a suitable reference level for the MGMT protein was found to be 150 amol/µg which is the lower limit of quantitation. However, the skilled artisan will recognize that levels higher or lower than these reference levels can be selected based on clinical results and experience.

Because both nucleic acids and protein can be analyzed from the same Liquid Tissue™ biomolecular preparation it is possible to generate additional information about disease diagnosis and drug treatment decisions from the nucleic acids in same sample upon which proteins were analyzed. For example, if the MGMT protein is expressed by certain cells at increased/decreased levels, when assayed by SRM the data can provide information about the state of the cells and their potential for uncontrolled growth, choice of optimal therapy, and potential drug resistance. At the same time, information about the status of genes and/or the nucleic acids and proteins they encode (e.g., mRNA molecules and their expression levels or splice variations) can be obtained from nucleic acids present in the same Liquid Tissue biomolecular preparation. Nucleic acids can be assessed simultaneously to the SRM analysis of proteins, including the MGMT protein. In one embodiment, information about the MGMT protein and/or one, two, three, four or more additional proteins may be assessed by examining the nucleic acids encoding those proteins. Those nucleic acids can be examined, for example, by one or more, two or more, or three or more of: sequencing methods, polymerase chain reaction methods, restriction fragment polymorphism analysis, identification of deletions, insertions, and/or determinations of the presence of mutations, including but not limited to, single base pair polymorphisms, transitions, transversions, or combinations thereof.

In one embodiment, a method of treating a patient suffering from glioblastoma cancer is provided herein comprising:

(a) quantifying the level of a specified MGMT fragment peptide, such as SEQ ID NO:1, in a protein digest prepared from a tumor sample, such as an FFPE tumor sample, obtained from the patient and calculating the level of the MGMT fragment peptide in said sample by selected reaction monitoring using mass spectrometry;

(b) comparing the level of said MGMT fragment peptide to a reference level, such as about 150 amol/m, and (c) treating the patient with a therapeutic regimen comprising an effective amount of the chemotherapeutic agent temozolomide when the level of the MGMT fragment peptide is lower than said reference level, and optionally (d) treating the patient with a therapeutic regimen that does not comprise an effective amount of the chemotherapeutic agent temozolomide when the level of the MGMT fragment peptide is above said reference level.

EXAMPLES

Example 1: Determination of a Predictive Value of MGMT Protein Expression for Temozolomide Sensitivity/Resistance in a Population of GBM Patients Patients 22 patients were identified with glioblastoma (GBM). Tumors were surgically removed prior to treatment and archived as formalin-fixed, paraffin-embedded (FFPE) tissue and all were histologically glioblastoma. All 22 patients were subsequently treated with temozolomide.

Methods

Archived formalin-fixed, paraffin-embedded tissue sections were obtained from patients with GBM treated with temozolomide (n=22). A board-certified pathologist marked the tumor areas. Based on the markups, tumor cells were laser microdissected and solubilized to tryptic peptides using the Liquid Tissue™ process. In each liquefied sample, multiple protein biomarkers including MGMT were quantified with selected reaction monitoring (SRM) mass spectrometry (MS). A mixture of stable isotope-labeled heavy peptides including MGMT was added prior to MS analysis. Each sample was analyzed in triplicate. A MGMT cutoff of 150 amol/µg protein analyzed was based on the limit of quantitation from a concentration curve.

Results

The MGMT fragment peptide, SEQ ID NO:1, was detected and GBM patients with MGMT protein levels below a cutoff of 150 amol/µg (n=19) had greater median progression-free survival (PFS) as patients with MGMT levels above the cutoff (p=0.040). Results indicated a correlation of increased MGMT protein expression with a negative therapeutic outcome by treatment of the cancer patient with temozolomide as evidenced by decreased progression-free survival after initial diagnosis and initiation of treatment regime with temozolomide (FIG. 1). Likewise, lower levels of MGMT correlated with a positive therapeutic outcome as evidenced by increased progression-free survival from treatment with temozolomide (FIG. 1). Results are shown as probability (0-100%) for progression-free survival in months after initiation of treatment. The Mantel-Cox log-rank and Gehan-Breslow-Wilcoxon tests were used for survival comparisons. Quantitative levels of other analyzed proteins did not correlate with a negative/positive outcome to treatment with temozolomide.

an effective amount of a proteolytic enzyme selected from the group consisting of trypsin, chymotrypsin, and endoproteinase Lys-C for a period of time from 30 minutes to 24 hours at a temperature from 37° C. to 65° C.

6. The method of claim 5, wherein the protein digest of the formalin-fixed glioblastoma tumor sample comprises a trypsin digest.

7. The method of claim 1, wherein the mass spectrometry comprises tandem mass spectrometry, ion trap mass spectrometry, triple quadrupole mass spectrometry, MALDI-TOF mass spectrometry, MALDI mass spectrometry, hybrid ion trap/quadrupole mass spectrometry and/or time of flight mass spectrometry.

8. The method of claim 7, wherein a mode of mass spectrometry used is Selected Reaction Monitoring (SRM), Multiple Reaction Monitoring (MRM), Parallel Reaction Monitoring (PRM), intelligent Selected Reaction Monitoring (iSRM), and/or multiple Selected Reaction Monitoring (mSRM).

9. The method of claim 1, wherein the formalin-fixed glioblastoma tumor sample is a cell, collection of cells, or a solid tissue.

10. The method of claim 9, wherein the formalin-fixed glioblastoma tumor sample is a solid tissue.

11. The method of claim 10, wherein the formalin-fixed solid tissue is paraffin embedded tissue.

12. The method of claim 1, further comprising detecting the MGMT fragment peptide according to SEQ ID NO:1 and quantifying the MGMT fragment peptide according to SEQ

What is claimed is:

1. A method of treating a patient suffering from glioblastoma cancer comprising: administering to the patient an effective amount of temozolomide, wherein a mass spectrometry analysis of a protein digest of a formalin-fixed glioblastoma tumor sample from the patient evidences an amount of a MGMT fragment peptide according to SEQ ID NO:1 less than or equal to 150 amol/µg.

2. The method of claim 1, wherein the protein digest of the formalin-fixed glioblastoma tumor sample from the patient evidences an amount of the MGMT fragment peptide according to SEQ ID NO:1 less than or equal to 100 amol/µg.

3. The method of claim 2, wherein the protein digest of the formalin-fixed glioblastoma tumor sample from the patient evidences an amount of the MGMT fragment peptide according to SEQ ID NO:1 less than or equal to 50 amol/µg.

4. The method of claim 3, wherein the protein digest of the formalin-fixed glioblastoma tumor sample from the patient evidences an amount of the MGMT fragment peptide according to SEQ ID NO:1 less than or equal to 25 amol/µg.

5. The method of claim 1, wherein the protein digest of the formalin-fixed glioblastoma tumor sample is treated with ID NO:1 by determining the amount of the MGMT fragment peptide according to SEQ ID NO:1 in the sample by comparing to a spiked internal standard peptide of known amount, wherein both the MGMT fragment peptide according to SEQ ID NO:1 in the sample and the internal standard peptide correspond to the same amino acid sequence of SEQ ID NO:1.

13. The method of claim 12, wherein the internal standard peptide is an isotopically labeled peptide.

14. The method of claim 13, wherein the isotopically labeled internal standard peptide comprises one or more heavy stable isotopes selected from the group consisting of $^{18}O$, $^{17}O$, $^{15}N$, $^{13}C$, $^{2}H$ and a combination thereof.

15. The method of claim 14, wherein the detecting and the quantitating the MGMT fragment peptide according to SEQ ID NO:1 can be combined with detecting and quantitating other peptides from other proteins in multiplex so that a treatment decision about which agent used for treatment is based upon specific levels of the MGMT fragment peptide according to SEQ ID NO:1 in combination with other peptides/proteins in the sample.

16. The method of claim 1, further comprising administering to the patient, in addition to TMZ, an effective amount of one or more chemotherapy agents selected from the group consisting of cisplatin, carboplatin, xaliplatin, cyclophosphamide, melphalan and chlorambucil.

* * * * *

SEQUENCE LISTING

<160> NUMBER OF SEQ ID NOS: 1

<210> SEQ ID NO 1
<211> LENGTH: 9
<212> TYPE: PRT
<213> ORGANISM: Homo sapiens

<400> SEQUENCE: 1

Thr Thr Leu Asp Ser Pro Leu Gly Lys
1               5